(12) United States Patent
Miyazawa et al.

(10) Patent No.: US 8,367,082 B2
(45) Date of Patent: Feb. 5, 2013

(54) MICROGEL AND EXTERNAL COMPOSITIONS CONTAINING THE SAME

(75) Inventors: Kazuyuki Miyazawa, Yokohama (JP); Isamu Kaneda, Yokohama (JP); Toshio Yanaki, Yokohama (JP); Tadashi Nakamura, Yokohama (JP); Masatoshi Ochiai, Yokohama (JP); Tomoyuki Kawasoe, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 836 days.

(21) Appl. No.: 12/082,130

(22) Filed: Apr. 9, 2008

(65) Prior Publication Data

US 2009/0047312 A1 Feb. 19, 2009

Related U.S. Application Data

(63) Continuation of application No. 09/936,317, filed on Nov. 6, 2001, now abandoned.

(30) Foreign Application Priority Data

| Jan. 11, 2000 | (JP) | 2000-002610 |
| Jan. 11, 2000 | (JP) | 2000-002611 |
| Mar. 30, 2000 | (JP) | 2000-094307 |
| Mar. 30, 2000 | (JP) | 2000-094308 |

(51) Int. Cl.
*A61K 8/02* (2006.01)
*A61Q 5/00* (2006.01)

(52) U.S. Cl. ........ 424/401; 426/575; 424/484; 424/70.1

(58) Field of Classification Search .................. None
See application file for complete search history.

(56) References Cited

U.S. PATENT DOCUMENTS 5,360,624 A * 11/1994 Okura et al. ............... 426/573
2002/0006414 A1 * 1/2002 Murata et al. .............. 424/400

FOREIGN PATENT DOCUMENTS

EP 911017 A2 * 4/1999

* cited by examiner

*Primary Examiner* — Michael G Hartley
*Assistant Examiner* — Nabila Ebrahim
(74) *Attorney, Agent, or Firm* — Andrew F. Young, Esq.; Lackenbach Siegel, LLP

(57) ABSTRACT

The present invention provides a microgel having a mean particle size of 0.1-1,000 μm, the microgel being produced from a gel which is formed by use of a hydrophilic compound capable of forming a gel. An external composition containing the microgel provides an excellent sensation during use; i.e., the composition provides neither sticky sensation during use nor frictional sensation. Furthermore, even when a large amount of a pharmaceutical ingredient, such as a whitening ingredient, or a salt is incorporated into the composition, the viscosity of the composition is not lowered, and the composition exhibits excellent viscosity increasing property. In addition, the composition exhibits long-term stability, without inviting separation of water.

20 Claims, No Drawings

MICROGEL AND EXTERNAL COMPOSITIONS CONTAINING THE SAME

TECHNICAL FIELD

The present invention relates to a viscosity control agent which is used mainly in the fields of, for example, cosmetic compositions and drugs. The present invention also relates to external compositions, such as cosmetic compositions, comprising the viscosity control agent.

BACKGROUND ART

Conventionally known methods for increasing the viscosity of an external composition include a method for incorporating into the composition a viscosity control agent or a thickening agent; for example, a polysaccharide such as xanthan gum, a hydrophilic synthetic polymer such as a polyacrylic acid, or a clay mineral such as bentonite.

When a polysaccharide such as xanthan gum is incorporated, as a viscosity control agent, into an external composition, the composition involves problems in terms of sensation during use; for example, the composition provides a sticky sensation during use, although such a polysaccharide exhibits excellent stability in the composition into which a pharmaceutical ingredient or a salt is incorporated. When a hydrophilic synthetic polymer such as polyacrylic acid is incorporated into an external composition, the composition provides good sensation during use; i.e., the composition provides no sticky sensation during use, but provides a refreshing sensation during use. However, such a hydrophilic synthetic polymer has low resistance to a salt or an ionic substance. Therefore, when a large amount of a salt or a pharmaceutical ingredient such as a whitening ingredient; for example, L-ascorbic acid (i.e., vitamin C) or arbutin, is incorporated into the composition, the composition involves problems including lowering of the viscosity of the composition. When a clay mineral such as bentonite is incorporated, as a viscosity control agent, into an external composition, the composition involves problems in terms of sensation during use; for example, the composition provides a frictional sensation during use.

An object of the present invention is to provide a new type of viscosity control agent which, when incorporated as an ingredient into an external composition, imparts the composition with excellent sensation during use; i.e., free of sticky sensation or frictional sensation. Furthermore, even when a large amount of a salt or a pharmaceutical ingredient such as a whitening ingredient is incorporated into the composition, the viscosity of the composition is not lowered, the composition exhibits long-term stability, and separation of water does not occur. Another object of the present invention is to provide an external composition comprising the viscosity control agent.

DISCLOSURE OF THE INVENTION

The present inventors have performed extensive studies in order to attain the aforementioned objects, and have found that, when a compound capable of forming a gel, such as agar which is conventionally used as a gelation agent, is formed into a gel, the resultant gel is pulverized into a microgel, and then the resultant microgel is incorporated, as a viscosity control agent, into an external composition, the composition provides no sticky sensation during use, and the viscosity of the composition is not lowered even when a large amount of pharmaceutical ingredient such as a whitening ingredient or large amounts of various salts are incorporated into the composition. The present invention has been accomplished on the basis of this finding.

Accordingly, the present invention provides a microgel having a mean particle size of 0.1-1,000 μm, the microgel being produced from a gel which is formed by use of a hydrophilic compound capable of forming a gel (hereinafter the microgel may be referred to as "the present microgel").

The present microgel may be produced through a process comprising dissolving, in an aqueous solvent, a hydrophilic compound capable of forming a gel; forming a gel; and pulverizing the gel into a microgel having a mean particle size of 0.1-1,000 μm (hereinafter the process may be referred to as "the present production process").

The present invention also provides an external composition comprising the present microgel (hereinafter the composition may be referred to as "the present external composition"). In the external composition of the present invention, a salt or a pharmaceutical ingredient such as a whitening ingredient may be incorporated intentionally.

As used herein, the term "external composition" refers to a composition which is applied onto the skin (including the scalp and hair). The composition can be used to prepare, for example, cosmetic compositions, hair-dyes, external drugs, and external quasi-drugs.

BEST MODE FOR CARRYING OUT THE INVENTION

Embodiments of the present invention will next be described.

No particular limitation is imposed on the hydrophilic compound capable of forming a gel which is used for producing the present microgel, so long as the compound is a water-soluble compound capable of forming a gel and can be incorporated into an external composition. Specific examples of the hydrophilic compound include hydrophilic proteins capable of forming a gel, such as gelatin and collagen; and hydrophilic polysaccharides such as agar, curdlan, scleroglucan, schizophyllan, gellan gum, alginic acid, carrageenan, mannan, pectin, and hyaluronic acid. Of these, gelatin, agar, curdlan, gellan gum, alginic acid, or carrageenan is particularly preferred, since such a compound is not easily affected by a salt or an ionic substance in the composition, and enables to provide a stable gel. One or more of these gel-formable hydrophilic compounds may be used.

The present microgel may be produced through, for example, the below-described process (i.e., the present production process).

Firstly, any of the aforementioned hydrophilic compounds capable of forming a gel is dissolved in an aqueous solvent such as water, and is allowed to form a gel. The hydrophilic compound may be dissolved in an aqueous solvent through a customary method; for example, through mixing or heating. Gelation (solidification) is preferably carried out by stopping heating of the resultant mixture after dissolving, and then allowing the mixture to stand still until the temperature of the mixture becomes lower than the gelation temperature (solidification temperature).

The aqueous solvent is not particularly limited, so long as the solvent can be incorporated into an external composition. Examples of the aqueous solvent include water; glycols such as 1,3-butylene glycol and propylene glycol; and lower alcohols such as ethanol and propanol. One or more of such aqueous solvents may be used. Water or a mixture of water and another aqueous solvent is preferably used.

The aqueous solvent may contain a water-soluble ingredient other than the aqueous solvent, which ingredient can be incorporated into an external composition. Specific examples of the water-soluble ingredient include, but are not limited to, chelating agents such as metaphosphates and edetates; pH-adjusting agents; preservatives; water-soluble pharmaceutical ingredients; and salts.

The gel strength of the aforementioned gel is not particularly limited, so long as the gel can maintain its shape and the gel can be subjected to the subsequent procedure to thereby form a microgel. In the present invention, a gel having a very high gel strength; for example, a gel having a high jelly strength (as measured according to the official method of Japanese Association of Agar) of up to 1,000 g/cm$^2$ or thereabouts, can be used. Meanwhile, a gel having a very low jelly strength (i.e., a jelly strength of 30 g/cm$^2$ or thereabouts) can also be formed into a microgel. From the viewpoint of enhancement of sensation during use, a gel having a jelly strength of 100 g/cm$^2$ or thereabouts is preferred.

In order to vary sensation during use of the present external composition, a viscosity increasing compound incapable of forming a gel may be incorporated into the present external composition in addition to the aforementioned hydrophilic compound capable of forming a gel. Examples of the viscosity increasing compound incapable of forming a gel include hydrophilic viscosity increasing compounds including hydrophilic synthetic polymers such as polyacrylic acid, polyethylene glycol, polyacrylamide, polyalkylacrylamide/polyacrylamide copolymers, carboxymethyl cellulose, cationized cellulose, and pluronic; hydrophilic naturally-occurring polymers such as xanthan gum, succinoglycan, guar gum, and locust bean gum; and hydrophilic clay minerals such as laponite, bentonite, and smectite. When such a hydrophilic viscosity increasing compound incapable of forming a gel is used in combination with the hydrophilic compound capable of forming a gel, the gel strength of the resultant gel can be arbitrarily regulated. When the amount of the viscosity increasing compound incapable of forming a gel in the resultant gel is increased, the gel strength is lowered. The viscosity increasing compound incapable of forming a gel is particularly preferably xanthan gum, succinoglycan, polyacrylic acid, polyethylene glycol, polyacrylamide, or a polyalkylacrylamide/polyacrylamide copolymer. A salt of the viscosity increasing compound is also preferably used. One or more of the viscosity increasing compounds incapable of forming a gel may be used.

The incorporation amount of the hydrophilic viscosity increasing compound incapable of forming a gel varies with intended use of the resultant viscosity control agent. The viscosity increasing compound incapable of forming a gel may be incorporated in an amount of about 1-100 mass % based upon the hydrophilic compound capable of forming a gel.

Subsequently, the gel formed as described above is pulverized (crushed) by means of, for example, a homogenizer, a high speed mixer, or a mechanical stirrer, to thereby obtain a desired microgel. The mean particles size of the microgel is preferably about 0.1-1,000 µm, more preferably about 1-300 µm, much more preferably about 10-200 µm. The degree of pulverization of the gel may be regulated in accordance with use of the microgel. When the microgel is required to have a smooth sensation during use, the gel is sufficiently pulverized through high-speed stirring, to thereby obtain a microgel having a very small particle size. When an intrinsic tactile sensation of the microgel is required, the degree of pulverization of the gel is decreased through low-speed or brief stirring, to thereby obtain a microgel having a slightly large particle size.

The viscosity of the thus-obtained microgel varies in accordance with use or need of the microgel. For example, when agar is used as the hydrophilic compound capable of forming a gel, the viscosity of the resultant microgel (agar content: about 0.5-2%) is preferably about 2,000-1,000,000 mPa·s, the viscosity being measured by use of a B-type viscometer (revolution number: 0.6 rpm, at 25° C.).

When the microgel produced by the present invention is incorporated, as a viscosity control agent, into an external composition, improvement of sensation during use of the composition (i.e., suppression of a sticky sensation during use) can be attained. Even when a pharmaceutical ingredient, salt, etc. is incorporated into the external composition in a large amount; for example, in an amount of about 20 mass % of the total of the composition, the viscosity of the composition is not lowered; i.e., the viscosity of the composition can be maintained. Furthermore, the composition exhibits long-term stability, and separation of water does not occur. The amount of a pharmaceutical ingredient or a salt incorporated into the composition is preferably about 0.1 mass % or more of the total of the composition, in order to obtain the intended effects of incorporation of such an ingredient.

The present external composition may contain a water-soluble or oil-soluble pharmaceutical ingredient or salt.

A pharmaceutical ingredient is incorporated into the external composition in order to impart effective pharmaceutical activity to the composition. Most pharmaceutical ingredients have a variety of active groups, and assume a salt form. Therefore, when a large amount of such a pharmaceutical ingredient is incorporated into the composition, the stability of a composition may be impaired. Examples of the pharmaceutical ingredient which may be incorporated into the composition include vitamins, anti-inflammatory agents, antibacterial agents, and whitening ingredients. Specific examples of the pharmaceutical ingredient include vitamins and derivatives thereof, such as vitamin B, vitamin P, water-soluble vitamin A, and water-soluble vitamin D; pantothenyl ethyl ether; calcium pantothenate; glycyrrhizic acid; glycyrrhizinates; glycyrrhetic acid; glycyrrhetinates; royal jelly; polyphenol; nicotinic acid and derivatives thereof (e.g., nicotinamide); resorcin; sulfur; salicylic acid and derivative thereof; urea; xylitol; trehalose; and caffeine. One or more of the pharmaceutical ingredients may be incorporated into the present external composition.

Preferred examples of the whitening ingredient include L-ascorbic acid and derivatives thereof; arbutin; glutathione; tranexamic acid and derivatives thereof; placenta extract; and vegetable extracts exhibiting whitening effects (e.g., chamomile extract, *Scutellaria* root extract, and *Saxifraga* extract).

L-ascorbic acid is generally called "vitamin C," exhibits cell respiration effects, enzyme activation effects, and collagen formation effects, due to its strong reducing effects, and exhibits melanin-reducing effects. Examples of L-ascorbic acid derivatives include L-ascorbic acid monoalkyl esters such as L-ascorbyl monostearate, L-ascorbyl monopalmitate, and L-ascorbyl monooleate; L-ascorbic acid monoesters such as L-ascorbyl monophosphate and L-ascorbyl-2-sulfate; L-ascorbic acid dialkyl esters such as L-ascorbyl distearate, L-ascorbyl dipalmitate, and L-ascorbyl dioleate; L-ascorbic acid diesters such as L-ascorbyl diphosphate; L-ascorbic acid trialkyl esters such as L-ascorbyl tristearate, L-ascorbyl tripalmitate, and L-ascorbyl trioleate; ascorbic acid triesters such as L-ascorbyl triphosphate; L-ascorbic acid glucoside such as L-ascorbic acid 2-glucoside; and salts thereof. Of the L-ascorbic acid and derivatives thereof, L-ascorbic acid, L-ascorbyl phosphate, L-ascorbyl-2-sulfate, L-ascorbic acid 2-glucoside, or a salt thereof is preferably used.

Examples of tranexamic acid derivatives include dimers of tranexamic acid (e.g., trans-4-(trans-aminomethylcyclohexanecarbonyl) aminomethylcyclohexanecarboxylic acid hydrochloride); esters of tranexamic acid and hydroquinone (e.g., 4'-hydroxyphenyl trans-4-aminomethylcyclohexanecarboxylate); esters of tranexamic acid and gentisic acid (e.g., 2-(trans-4-aminomethylcyclohexylcarbonyloxy)-5-hydroxybenzoic acid and salts thereof); and amides of tranexamic acid (e.g., trans-4-aminomethylcyclohexanecarboxylic acid methylamide and salts thereof, trans-4-(P-methoxybenzoyl)aminomethylcyclohexanecarboxylic acid and salts thereof, and trans-4-guanidinomethylcyclohexanecarboxylic acid and salts thereof).

Similar to the case of other pharmaceutical ingredients, one or more of the whitening ingredients may be used.

The amount of the whitening ingredient incorporated into the present external composition is preferably about 0.1-20 mass %, more preferably about 0.5-5 mass %, of the total of the composition.

Examples of salts include a variety of pharmaceutically acceptable organic acid salts, amino acid salts, and inorganic salts. Examples of the organic acid salts include hydrochlorides, metallic salts (e.g., sodium salts and potassium salts), and amine salts of organic acids such as citric acid, lactic acid, oxalic acid, and sulfonic acid. Examples of the amino acid salts include hydrochlorides, metallic salts (e.g., sodium salts and potassium salts), and amine salts of amino acids such as glycine, alanine, proline, lysine, aspartic acid, and glutamic acid. Examples of inorganic salts include sodium salts, potassium salts, magnesium salts, calcium salts, carbonates, phosphates, nitrates, borates, sulfates, sulfites, and halogen compounds (e.g., sodium chloride and potassium chloride).

The present external composition exhibits excellent resistance to a salt. Therefore, even when a large amount of the aforementioned salt or a salt of the aforementioned pharmaceutical ingredient is incorporated into the composition, the stability of the composition is not impaired, and the composition provides an excellent sensation during use as described above.

Conventionally, a compound capable of forming a gel, such as agar, carrageenan, curdlan, or gelatin, has been used as a viscosity control agent. In this case, such a compound is heated and dissolved in an external composition, and the resultant mixture is gradually cooled under stirring, to thereby obtain a viscous composition without solidification (gelation) of the compound (e.g., Japanese Patent Application Laid-Open (kokai) No. 11-209262). However, when the external composition containing the compound capable of forming a gel is gradually cooled under stirring as described in the conventional method, to thereby increase the viscosity of the composition, the degree of increase in the viscosity of the composition is limited. Particularly when a pharmaceutical ingredient or a salt is incorporated into the external composition, the viscosity of the composition is prone to decrease.

In contrast, in the present invention, after such a compound capable of forming a gel is subjected to complete gelation (solidification), the gelled compound is pulverized into a microgel, and the resultant microgel is used as a viscosity control agent. The present microgel obtained as described above differs from a polysaccharide viscosity control agent or a synthetic polymer viscosity control agent which is conventionally used in an external composition such as a cosmetic composition, in that the present microgel exerts the viscosity increasing effect not through entanglement of molecules but through friction of the microgel particles yielded from pulverization of the gel. Therefore, the present microgel does not exhibit spinnability that is unique to polymer solutions, and an external composition containing the microgel provides a very refreshing sensation during use. Also, as contrasted to polymer solutions, which in some cases are affected by a pharmaceutical ingredient or salt incorporated therein to thereby lower the viscosity and impose limitations on incorporation of the pharmaceutical ingredient or salt, the present invention is free from such problems, permitting a variety of external compositions, including cosmetic compositions, to be formulated.

In the present invention, when a water-soluble pharmaceutical ingredient or salt is used, after the aforementioned hydrophilic ingredient capable of forming a gel is dissolved in an aqueous solvent, the resultant mixture is allowed to stand and cool, for example, to thereby form a gel, and subsequently, a microgel obtained by pulverizing the resultant gel may be mixed with the pharmaceutical ingredient or salt. Alternatively, after the aforementioned hydrophilic ingredient and the pharmaceutical ingredient or salt are dissolved in an aqueous solvent, the resultant mixture is allowed to stand and cool, for example, to thereby form a gel, and subsequently the resultant gel may be pulverized into a microgel.

When an oil-soluble pharmaceutical ingredient or salt is used, after the aforementioned hydrophilic ingredient capable of forming a gel is dissolved in an aqueous solvent, the resultant mixture is allowed to stand and cool, for example, to thereby form a gel, and subsequently, the resultant gel may be pulverized into a microgel. Separately, the oil-soluble pharmaceutical ingredient or salt and another oil ingredient are preferably preliminarily emulsified in an aqueous system, and the resultant emulsion is mixed with the above-obtained microgel, and the resultant mixture is emulsified.

The present external composition containing the present microgel may appropriately contain an ingredient which is generally incorporated into an external composition such as a cosmetic composition, such as a humectant, a preservative, powder, a colorant, a perfume, or a pH-adjusting agent, so long as the ingredient does not impede the purposes and the effects of the present invention.

The present microgel may be incorporated into an aqueous external composition, or, similar to the case of a usual polymer viscosity control agent, may be incorporated into an emulsified external composition such as a milky lotion or a cream. The present microgel may be incorporated into an external composition even when the product form of the composition is a hair-setting agent, a hair cream, a body-care product, or hair dye. For example, when the present microgel is incorporated into an acidic hair dye, the stability, the adhesive property, and the usability of the hair dye can be enhanced. In addition, the present microgel per se can be used as a gel-type external composition.

EXAMPLES

The present invention will next be described in more detail by way of Examples, which should not be construed as limiting the invention thereto.

Examples 1 Through 10 and Comparative Examples 1 Through 4

External compositions containing ingredients shown in the below-described Tables 1 (1-1 and 1-2) and 2 (2-1 and 2-2) were prepared as follows.

Examples 1 through 10

A hydrophilic compound capable of forming a gel and a viscosity increasing compound incapable of forming a gel were added to water, mixed, heated to 90° C., dissolved, and then allowed to stand at room temperature, to thereby form a gel. Subsequently, the gel was pulverized with a homogenizer, to thereby yield a microgel having a mean particle size of 100 μm. The microgel was mixed with the remaining ingredients, and the resultant mixture was stirred, to thereby yield the external compositions of Examples 1 through 10.

Comparative Examples 1 through 4

The ingredients were mixed, and then allowed to stand for 12 hours at room temperature, to thereby yield external compositions of Comparative Examples 1 through 4.

On the basis of the below-described evaluation criteria, the external composition (sample) of each of Examples 1 through 10 and Comparative Examples 1 through 4 was evaluated in terms of viscosity increasing effect, sensation during use (no sticky sensation during use), whitening effect, and long-term stability. The results are also shown in Tables 1 and 2. "Sodium polyacrylate" shown in Tables 1 and 2 was prepared by neutralizing "Hiviswako 105" (product of Wako Pure Chemical Industries, Ltd.) with an aqueous solution of sodium hydroxide and adjusting pH of the resultant solution to 7.

[Viscosity Increasing Property]

The viscosity of the above-obtained sample was measured by use of a B-type viscometer (number of revolution: 0.6 rpm, at 25° C.), to thereby evaluate the viscosity increasing property of the sample.

(Evaluation)

A: very excellent viscosity increasing property (viscosity: 50,000 mPa·s or more)

B: excellent viscosity increasing property (viscosity: 5,000 to 50,000 mPa·s)

C: poor viscosity increasing property (viscosity: 500 to 5,000 mPa·s)

D: no viscosity increasing property (viscosity: less than 500 mPa·s)

[Sensation During Use (No Sticky Sensation During Use)]

Each sample was actually used by 20 female panelists, and sensation during use of the sample was evaluated on the basis of the following criteria.

(Evaluation)

A: 18 or more of the panelists reported that the sample provided no sticky sensation during use but a refreshing sensation during use B: 15 to 17 of the panelists reported that the sample provided no sticky sensation during use but a refreshing sensation during use C: 6 to 14 of the panelists reported that the sample provided no sticky sensation during use but a refreshing sensation during use D: 5 or fewer of the panelists reported that the sample provided no sticky sensation during use but a refreshing sensation during use.

[Whitening Effect]

Each sample was used by 20 female panelists consecutively for two weeks, and the whitening effect of the sample was evaluated on the basis of the following criteria.

(Evaluation)

A: 18 or more of the panelists reported that the sample exhibited excellent whitening effect B: 15 to 17 of the panelists reported that the sample exhibited excellent whitening effect C: 6 to 14 of the panelists reported that the sample exhibited excellent whitening effect D: 5 or fewer of the panelists reported that the sample exhibited excellent whitening effect.

[Long-Term Stability (No Separation of Water)]

After the sample was stored at 40° C. for one month, the degree of separation of water was visually observed, and the long-term stability of the sample was evaluated on the basis of the following criteria.

(Evaluation)

A: no separation of water was observed

B: little separation of water was observed

C: slight oozing of water was observed

D: oozing of water was observed.

TABLE 1-1

|  | Ex. 1 | Ex. 2 | Ex. 3 | Ex. 4 | Ex. 5 | Ex. 6 | Ex. 7 |
|---|---|---|---|---|---|---|---|
|  | Amount (mass %) | | | | | | |
| Agar | 1.0 | 2.0 | — | — | — | 1.0 | 1.0 |
| Carrageenan | — | — | 1.5 | — | — | — | — |
| Curdlan | — | — | — | 3.0 | — | — | — |
| Gelatin | — | — | — | — | 3.0 | — | — |
| Gellan gum | — | — | — | — | — | — | — |
| Alginic acid | — | — | — | — | — | — | — |
| Xanthan gum | — | — | 0.1 | — | 0.1 | 0.1 | — |
| Succinoglycan | — | — | — | 0.1 | — | — | 0.2 |
| Sodium polyacrylate | 0.1 | — | — | — | — | — | — |
| Polyethylene glycol (M.W. = 20,000) | — | — | — | — | — | — | — |
| Polyacrylamide (M.W. = 1,000,000) | — | 0.1 | — | — | — | — | — |
| Polyalkylacrylamide/ Polyacrylamide copolymer (M.W. = 500,000) | — | — | — | — | — | — | — |
| Arbutin | 3.0 | — | — | — | 3.0 | — | — |

TABLE 1-2

|  | Ex. 1 | Ex. 2 | Ex. 3 | Ex. 4 | Ex. 5 | Ex. 6 | Ex. 7 |
|---|---|---|---|---|---|---|---|
|  | Amount (mass %) | | | | | | |
| L-Ascorbic acid | 0.2 | — | — | — | — | 2.0 | — |
| L-Ascorbic acid 2-glucoside | — | 2.0 | — | — | — | — | 2.0 |
| Magnesium L-ascorbyl phosphate | — | — | 3.0 | — | — | — | — |
| Gultathione | — | — | 0.1 | 0.1 | — | 0.2 | — |
| Tranexamic acid | — | — | — | 0.3 | — | — | 0.5 |
| Placenta extract | — | 0.1 | — | — | — | — | — |

TABLE 1-2-continued

|  | Ex. 1 | Ex. 2 | Ex. 3 | Ex. 4 | Ex. 5 | Ex. 6 | Ex. 7 |
|---|---|---|---|---|---|---|---|
|  | Amount (mass %) | | | | | | |
| Chamomile extract | — | 0.1 | — | — | — | — | — |
| CaCl$_2$ | — | — | — | — | — | — | — |
| Glycerin | 5.0 | 5.0 | 5.0 | 5.0 | 5.0 | 5.0 | 5.0 |
| Purified water | Balance | Balance | Balance | Balance | Balance | Balance | Balance |
| Preparation method*⁾ | (1) | (1) | (1) | (1) | (1) | (1) | (1) |
| Viscosity-increasing property | A | A | A | A | A | A | A |
| (viscosity/mPa · s) × 10$^3$ | (120) | (395) | (135) | (205) | (65) | (120) | (135) |
| Sensation during use | A | A | A | A | A | A | A |
| Whitening effect | A | A | A | B | A | A | A |
| Long-term stability | A | A | A | A | A | A | A |

Preparation method*⁾ = (1) Pulverization after gelation; (2) Mixing only

TABLE 2-1

|  | Ex. 8 | Ex. 9 | Ex. 10 | Comp. Ex. 1 | Comp. Ex. 2 | Comp. Ex. 3 | Comp. Ex. 4 |
|---|---|---|---|---|---|---|---|
|  | Amount (mass %) | | | | | | |
| Agar | 1.0 | — | — | — | — | — | — |
| Carrageenan | — | — | — | — | — | — | — |
| Curdlan | — | — | — | — | — | — | — |
| Gelatin | — | — | — | — | — | — | — |
| Gellan gum | — | 0.5 | — | — | — | — | — |
| Alginic acid | — | — | 2.0 | — | — | — | — |
| Xanthan gum | — | 0.2 | 0.2 | — | — | 0.5 | 1.0 |
| Succinoglycan | 0.1 | — | — | — | — | — | — |
| Sodium polyacrylate | — | — | — | 0.25 | 0.5 | — | — |
| Polyethylene glycol (M.W. = 20,000) | — | 0.2 | — | — | — | — | — |
| Polyacrylamide (M.W. = 1,000,000) | — | — | — | — | — | — | — |
| Polyalkylacrylamide/ polyacrylamide copolymer (M.W. = 500,000) | — | — | 0.1 | — | — | — | — |
| Arbutin | — | 3.0 | — | — | — | 3.0 | — |

TABLE 2-2

|  | Ex. 8 | Ex. 9 | Ex. 10 | Comp. Ex. 1 | Comp. Ex. 2 | Comp. Ex. 3 | Comp. Ex. 4 |
|---|---|---|---|---|---|---|---|
|  | Amount (mass %) | | | | | | |
| L-Ascorbic acid | — | 0.2 | — | — | — | — | — |
| L-Ascorbic acid 2-glucoside | — | — | 2.0 | 2.0 | — | — | 2.0 |
| Magnesium L-ascorbyl phosphate | 3.0 | — | — | — | 3.0 | — | — |
| Gultathione | — | — | 0.1 | 0.1 | — | — | — |
| Tranexamic acid | — | — | — | — | 0.1 | — | — |
| Placenta extract | 0.1 | — | — | — | — | 0.1 | — |
| Chamomile extract | 0.2 | — | — | — | — | — | 0.1 |
| CaCl$_2$ | — | 0.2 | — | — | — | — | — |
| Glycerin | 5.0 | 5.0 | 5.0 | 5.0 | 5.0 | 5.0 | 5.0 |
| Purified water | Balance | Balance | Balance | Balance | Balance | Balance | Balance |
| Preparation method*⁾ | (1) | (1) | (1) | (2) | (2) | (2) | (2) |
| Viscosity-increasing property | A | A | A | D | D | B | B |
| (viscosity/mPa · s) × 10$^3$ | (125) | (50) | (115) | (0.25) | (0.35) | (15) | (25) |
| Sensation during use | A | A | A | — | — | D | D |
| Whitening effect | A | A | A | — | — | A | A |
| Long-term stability | A | A | A | — | — | A | A |

Preparation method*⁾ = (1) Pulverization after gelation; (2) Mixing only

As is apparent from the results shown in Tables 1 and 2, even when the present external composition containing the present microgel contains a large amount of a whitening ingredient, the viscosity of the composition is not lowered. In addition, the present external composition exhibits excellent viscosity increasing property, provides good sensation during use; i.e., provides no sticky sensation during use, and exhibits excellent whitening effect and long-term stability.

Examples 11 Through 24 and Comparative Examples 5 Through 11

External compositions containing ingredients shown in the below-described Table 3 (3-1 and 3-2) through Table 5 (5-1 and 5-2) were prepared.

Specifically, an external composition of each of Examples 11 through 24 was prepared in manner similar to that of the external composition of each of Examples 1 through 10, and an external composition of each of Comparative Examples 5 through 11 was prepared in manner similar to that of the external composition of each of Comparative Examples 1 through 4.

The external composition of each of Examples 11 through 24 and Comparative Examples 5 through 11 was evaluated in terms of viscosity increasing effect, sensation during use (no sticky sensation during use), and long-term stability, on the basis of the above-described evaluation criteria. The results are shown in Tables 3 through 5. "Sodium polyacrylate" shown in Tables 3 through was prepared by neutralizing "Hiviswako 105" (product of Wako Pure Chemical Industries, Ltd.) with an aqueous solution of sodium hydroxide and adjusting pH of the resultant solution to 7.

TABLE 3-1

|  | Ex. 11 | Ex. 12 | Ex. 13 | Ex. 14 | Ex. 15 | Ex. 16 | Ex. 17 |
|---|---|---|---|---|---|---|---|
|  | Amount (mass %) | | | | | | |
| Agar | 1.0 | 2.0 | — | — | — | — | — |
| Carrageenan | — | — | 1.5 | — | — | — | — |
| Curdlan | — | — | — | 3.0 | — | — | — |
| Gelatin | — | — | — | — | 3.0 | — | — |
| Gellan gum | — | — | — | — | — | 1.0 | — |
| Alginic acid | — | — | — | — | — | — | 2.0 |
| Xanthan gum | 0.1 | — | 0.1 | — | 0.1 | 0.2 | 0.3 |
| Succinoglycan | — | 0.2 | — | 0.1 | — | — | — |
| Sodium polyacrylate | — | — | — | — | — | — | — |
| Polyethylene glycol (M.W. = 20,000) | — | — | — | — | — | — | — |
| Polyacrylamide (M.W. = 1,000,000) | — | — | — | — | — | — | — |
| Polyalkylacrylamide/ polyacrylamide copolymer (M.W. = 500,000) | — | — | — | — | — | — | — |

TABLE 3-2

|  | Ex. 11 | Ex. 12 | Ex. 13 | Ex. 14 | Ex. 15 | Ex. 16 | Ex. 17 |
|---|---|---|---|---|---|---|---|
|  | Amount (mass %) | | | | | | |
| NaCl | 2.0 | 2.0 | 2.0 | 2.0 | 2.0 | — | — |
| CaCl$_2$ | — | — | — | — | — | 0.5 | 0.5 |
| Glycine | — | — | — | — | — | 2.0 | 2.0 |
| Glycerin | 5.0 | 5.0 | 5.0 | 5.0 | 5.0 | 5.0 | 5.0 |
| Purified water | Balance | Balance | Balance | Balance | Balance | Balance | Balance |
| Preparation method*[)] | (1) | (1) | (1) | (1) | (1) | (1) | (1) |
| Viscosity-increasing property | A | A | A | A | A | A | A |
| (viscosity/mPa · s) × 10$^3$ | (115) | (395) | (135) | (205) | (60) | (75) | (120) |
| Sensation during use | A | A | A | A | A | A | A |
| Long-term stability | A | A | A | A | A | B | B |

Preparation method*[)] = (1) Pulverization after gelation; (2) Mixing only

TABLE 4-1

|  | Ex. 18 | Ex. 19 | Ex. 20 | Ex. 21 | Ex. 22 | Ex. 23 | Ex. 24 |
|---|---|---|---|---|---|---|---|
|  | Amount (mass %) | | | | | | |
| Agar | 2.0 | 2.0 | 2.0 | 2.0 | 2.0 | 2.0 | 2.0 |
| Carrageenan | — | — | — | — | — | — | — |
| Curdlan | — | — | — | — | — | — | — |
| Gelatin | — | — | — | — | — | — | — |
| Gellan gum | — | — | — | — | — | — | — |
| Alginic acid | — | — | — | — | — | — | — |
| Xanthan gum | — | — | — | — | 0.1 | 0.1 | 0.1 |
| Succinoglycan | — | — | — | — | — | — | — |
| Sodium polyacrylate | 0.1 | — | — | — | 0.1 | — | — |
| Polyethylene glycol (M.W. = 20,000) | — | 1.0 | — | — | — | — | — |
| Polyacrylamide (M.W. = 1,000,000) | — | — | 0.3 | — | — | 0.1 | — |
| Polyalkylacrylamide/ polyacrylamide copolymer (M.W. = 500,000) | — | — | — | 0.3 | — | — | 0.1 |

TABLE 4-2

|  | Ex. 18 | Ex. 19 | Ex. 20 | Ex. 21 | Ex. 22 | Ex. 23 | Ex. 24 |
|---|---|---|---|---|---|---|---|
|  | Amount (mass %) | | | | | | |
| NaCl | 5.0 | 5.0 | 2.0 | 5.0 | 5.0 | 5.0 | 5.0 |
| $CaCl_2$ | — | — | — | — | — | — | — |
| Glycine | — | — | — | — | — | — | — |
| Glycerin | 5.0 | 5.0 | 5.0 | 5.0 | 5.0 | 5.0 | 5.0 |
| Purified water | Balance | Balance | Balance | Balance | Balance | Balance | Balance |
| Preparation method*[)] | (1) | (1) | (1) | (1) | (1) | (1) | (1) |
| Viscosity-increasing property | A | A | A | A | A | A | A |
| (viscosity/mPa · s) × $10^3$ | (400) | (350) | (385) | (385) | (380) | (375) | (385) |
| Sensation during use | A | A | A | A | A | A | A |
| Long-term stability | A | A | A | A | A | A | A |

Preparation method*[)] = (1) Pulverization after gelation; (2) Mixing only

TABLE 5-1

|  | Comp. Ex. 5 | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|
|  | Amount (mass %) | | | | | | |
| Agar | — | — | — | — | — | — | — |
| Carrageenan | — | — | — | — | — | — | — |
| Curdlan | — | — | — | — | — | — | — |
| Gelatin | — | — | — | — | — | — | — |
| Gellan gum | — | — | — | — | — | — | — |
| Alginic acid | — | — | — | — | — | — | — |
| Xanthan gum | — | — | 0.5 | 1.0 | — | — | — |
| Succinoglycan | — | — | — | — | — | — | — |
| Sodium polyacrylate | 0.25 | 0.5 | — | — | — | — | — |
| Polyethylene glycol (M.W. = 20,000) | — | — | — | — | 1.0 | — | — |
| Polyacrylamide (M.W. = 1,000,000) | — | — | — | — | — | 0.3 | — |
| Polyalkylacrylamide/ polyacrylamide copolymer (M.W. = 500,000) | — | — | — | — | — | — | 0.3 |

TABLE 5-2

|  | Comp. Ex. 5 | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|
|  | Amount (mass %) | | | | | | |
| NaCl | 2.0 | 2.0 | 2.0 | 2.0 | — | — | — |
| $CaCl_2$ | — | — | — | — | — | — | — |
| Glycine | — | — | — | — | 2.0 | 2.0 | 2.0 |
| Glycerin | 5.0 | 5.0 | 5.0 | 5.0 | — | — | — |
| Purified water | Balance | Balance | Balance | Balance | Balance | Balance | Balance |
| Preparation method*[)] | (2) | (2) | (2) | (2) | (2) | (2) | (2) |
| Viscosity-increasing property | D | D | B | B | D | B | A |
| (viscosity/mPa · s) × $10^3$ | (0.25) | (0.35) | (15) | (25) | (0.12) | (15) | (105) |
| Sensation during use | — | — | C | D | — | C | C |
| Long-term stability | — | — | B | B | — | B | B |

Preparation method*[)] = (1) Pulverization after gelation; (2) Mixing only

As is apparent from the results shown in Tables 3 through 5, even when the present external composition containing the present microgel contains a large amount of a salt, the viscosity of the composition is not lowered. In addition, the present external composition exhibits excellent viscosity increasing property, provides good sensation during use; i.e., provides no sticky sensation during use, and exhibits excellent long-term stability.

Examples 25 and 26, Comparative Examples 12 and 13

Samples containing ingredients shown in the below-described Table 6 were prepared as follows.

Examples 25 and 26

Ingredients were mixed, heated to 90° C., dissolved, and then allowed to stand at room temperature, to thereby form a gel. The gel was pulverized with a homogenizer, to thereby yield a microgel (mean particle size: 100 μm).

Comparative Examples 12 and 13

Ingredients were mixed at 90° C., heating of the resultant mixture was stopped, and then the mixture was allowed to stand at room temperature.

Properties of the samples of Examples 25 and 26 and Comparative Examples 12 and 13 were evaluated. As shown in Table 6, the samples of Examples 25 and 26 exhibit consistency, and the samples of Comparative Examples 12 and 13 are gels (solid) having no consistency.

TABLE 6

|  | Ex. 25 | Ex. 26 | Comp. Ex. 12 | Comp. Ex. 13 |
| --- | --- | --- | --- | --- |
| Carrageenan | 1 | 2 | 1 | 2 |
| Glycerin | 5 | 5 | 5 | 5 |
| Purified water | Balance | Balance | Balance | Balance |
| Urea | 5 | 5 | 5 | 5 |
| Preparation method | Pulverization after gelation | Pulverization after gelation | Mixing under heat | Mixing under heat |
| Consistency | Yes | Yes | No | No |

Example 27, Comparative Example 14

O/W Cream

[Viscosity increasing agent A]

| Ingredient | Amount (mass %) |
| --- | --- |
| (1) Agar | 1.0 |
| (2) Keltrol | 0.1 |
| (3) Purified water | 98.9 |

<Preparation Method>

The above-listed ingredients (1) through (3) were mixed, dissolved at 90° C., and then cooled to form a gel. The gel was pulverized with a homogenizer, to thereby yield a microgel having a mean particle size of 100 µm (viscosity control agent A).

[Emulsion part A]

| Ingredient | Amount (mass %) |
| --- | --- |
| (1) Polyacrylic acid/polyalkylacrylate copolymer | 0.1 |
| (2) Polydimethylsiloxane (6 mPa · s) | 8.0 |
| (3) Potassium hydroxide | 0.1 |
| (4) Purified water | 91.8 |

<Preparation Method>

Ingredient (3) was added to ingredient (4), and to the resultant mixture were added ingredients (1) and (2), followed by mixing under stirring, to thereby yield emulsion part A.

Viscosity increasing agent A (50 mass %), ascorbic acid 2-glucoside (2 mass %), and emulsion part A (48 mass %) were mixed under stirring for emulsification, to thereby yield an O/W cream of Example 27.

Independently, ascorbic acid 2-glucoside (2 mass %) and emulsion part A (98 mass %) were mixed under stirring for emulsification, to thereby yield an O/W cream of Comparative Example 14.

The viscosity (25° C.) of each of the O/W creams prepared in Example 27 and Comparative Example 14 was measured by use of a B-type viscometer. The viscosity of the O/W cream of Example 27 and that of Comparative Example 14 were found to be 450,000 mPa·s and 20,000 mPa·s, respectively.

The results show that a compositional system which contains a pharmaceutical ingredient (whitening ingredient) and which fails to be thickened by a conventional viscosity control agent can be successfully thickened by the addition of the microgel of the present invention.

Example 28

Moisturizing Gel

| Ingredient | Amount (mass %) |
| --- | --- |
| (1) Glycerin | 7.0 |
| (2) Polyethylene glycol (PEG 1500) | 8.0 |
| (3) Agar | 2.0 |
| (4) Xanthan gum | 0.2 |
| (5) Ascorbic acid | 1.0 |
| (6) Tranexamic acid | 0.5 |
| (7) Citric acid | suitable amount |
| (8) Sodium citrate | suitable amount |
| (9) Sodium hydroxide | suitable amount |
| (10) Purified water | balance |
| (11) Preservative | suitable amount |
| (12) Antioxidant | suitable amount |
| (13) Perfume | suitable amount |

<Preparation Method>

Ingredients (3) and (4) were added to ingredient (10), and the resultant mixture was dissolved at 90° C. The solution was cooled to 50° C., and the remaining ingredients; i.e., (1), (2), (5) through (9), and (11) through (13) were added thereto. The mixture was cooled to a temperature at 30° C. or lower to cause gelation. When the mixture became sufficiently solidified, the gel was pulverized with a high speed mixer (mean particle size: 50 µm), followed by deaeration, yielding a moisturizing gel. The amounts of ingredients (7) through (9) were appropriately controlled so that the pH was adjusted to 7.

Example 29

Massage Cream (O/W)

| Ingredient | Amount (mass %) |
| --- | --- |
| (1) Solid paraffin | 5.0 |
| (2) Beeswax | 10.0 |
| (3) Vaseline | 15.0 |
| (4) Liquid paraffin | 31.0 |
| (5) Glycerin | 4.0 |
| (6) Glyceryl monostearate | 2.0 |
| (7) POE(20) sorbitan monolaurate | 2.0 |
| (8) Borax | 1.0 |
| (9) Carrageenan | 0.3 |
| (10) Succinoglycan | 0.1 |
| (11) Purified water | balance |
| (12) Gultathione | 0.1 |
| (13) Arbutin | 3.0 |
| (14) Preservative | suitable amount |
| (15) Antioxidant | suitable amount |
| (16) Perfume | suitable amount |

<Preparation Method>

Ingredient (8) was added to a portion of ingredient (11), and the resultant mixture was heated to 70° C. (aqueous phase). Oily ingredients (1) to (6) were heated to melt, followed by addition of ingredient (7) thereto, and the resultant mixture was maintained at 70° C. The thus-obtained oily mixture was added gradually to the aqueous phase for preliminary emulsification, followed by treatment with a homogenizing mixer, to thereby yield emulsion particles of uniform size (emulsion part).

Independently, in the remaining portion of ingredient (11), ingredients (9), (10), and (12) through (16) were dissolved at 90° C., and subsequently, the resultant mixture was cooled to form a gel. The thus-obtained gel was thoroughly pulverized with a homogenizing mixer, to thereby yield a microgel (mean particle size: 70 μm). The microgel was added to the above-prepared emulsion part, and the resultant mixture was subjected to stirring, deaeration, filtration, and cooling, to thereby yield a massage cream (O/W).

Example 30

O/W Cream

[Emulsion part B]

| Ingredient | Amount (mass %) |
| --- | --- |
| (1) Stearic acid | 8.0 |
| (2) Stearyl alcohol | 4.0 |
| (3) Butyl stearate | 6.0 |
| (4) Propylene glycol | 5.0 |
| (5) Glyceryl monostearate | 2.0 |
| (6) Potassium hydroxide | 0.4 |
| (7) Purified water | balance |

<Preparation Method>

To an aqueous phase (a mixture of ingredients (6) and (7)), ingredients (1) through (5) were added, followed by mixing under stirring, to thereby yield emulsion part B.

The thus-obtained emulsion part B (10 mass %), magnesium ascorbyl phosphate (3 mass %), and viscosity control agent A prepared in Example 27 (87 mass %) were mixed, to thereby yield an O/W cream.

Example 31

O/W Cream

[Emulsion part C]

| Ingredient | Amount (mass %) |
| --- | --- |
| (1) Solid paraffin | 5.0 |
| (2) Beeswax | 10.0 |
| (3) Vaseline | 15.0 |
| (4) Liquid paraffin | 41.0 |
| (5) 1,3-Butylene glycol | 4.0 |
| (6) Glyceryl monostearate | 2.0 |
| (7) POE(20) sorbitan monolaurate | 2.0 |
| (8) Boric acid | 0.2 |
| (9) Purified water | balance |

<Preparation Method>

To an aqueous phase (a mixture of ingredients (8) and (9)), ingredients (1) through (7) were added, followed by mixing under stirring, to thereby yield emulsion part C.

The thus-obtained emulsion part C (70 mass %), arbutin (2 mass %), and viscosity control agent A prepared in Example 27 (28 mass %) were mixed, to thereby yield an O/W cream.

Example 32

Pack

[Emulsion part D]

| Ingredient | Amount (mass %) |
| --- | --- |
| (1) Polyvinyl acetate emulsion | 15.0 |
| (2) Polyvinyl alcohol | 10.0 |
| (3) Sorbitol | 5.0 |
| (4) Polyethylene glycol (PEG 400) | 5.0 |
| (5) Jojoba oil | 4.0 |
| (6) POE sorbitan monostearate | 1.0 |
| (7) Titanium oxide | 5.0 |
| (8) Talc | 10.0 |
| (9) Ethanol | 10.0 |
| (10) Purified water | 37.0 |

<Preparation Method>

To an aqueous phase (a mixture of ingredients (9) and (10)), ingredients (1) through (8) were added, followed by mixing under stirring, to thereby yield emulsion part D.

The thus-obtained emulsion part D (80 mass %), ascorbic acid 2-glucoside (2 mass %), and viscosity control agent A prepared in Example 27 (18 mass %) were mixed, to thereby yield a pack.

The external compositions of the present invention prepared in Examples 27 through 32 were found to be endowed with excellent viscosity increasing property, and provided refreshing sensation during use with no sticky sensation. Moreover, the compositions were found to exhibit excellent whitening effect and long-term stability.

Example 33, Comparative Example 15

O/W Cream

Viscosity increasing agent A prepared in Example 27 (48 mass %), NaCl (2 mass %), and emulsion part A prepared in Example 27 (48 mass %) were mixed under stirring for emulsification, to thereby yield an O/W cream of Example 33.

Independently, NaCl (2 mass %) and emulsion part A prepared in Example 27 (98 mass %) were mixed under stirring for emulsification, to thereby yield an O/W cream of Comparative Example 15.

The viscosity (25° C.) of each of the O/W creams prepared in Example 33 and Comparative Example 15 was measured by use of a B-type viscometer. The viscosity of the O/W cream of Example 33 and that of Comparative Example 15 were found to be 400,000 mPa·s and 18,000 mPa·s, respectively.

The results show that a salt-containing compositional system which fails to be thickened by a conventional viscosity control agent can be successfully thickened by the addition of the microgel of the present invention.

Example 34

Massage Cream (O/W)

| Ingredient | Amount (mass %) |
|---|---|
| (1) Solid paraffin | 5.0 |
| (2) Beeswax | 10.0 |
| (3) Vaseline | 15.0 |
| (4) Liquid paraffin | 31.0 |
| (5) Glycerin | 4.0 |
| (6) Glyceryl monostearate | 2.0 |
| (7) POE(20) sorbitan monolaurate | 2.0 |
| (8) Borax | 1.0 |
| (9) Carrageenan | 0.3 |
| (10) Succinoglycan | 0.1 |
| (11) Purified water | balance |
| (12) Preservative | suitable amount |
| (13) Antioxidant | suitable amount |
| (14) Perfume | suitable amount |

<Preparation Method>

Ingredient (8) was added to a portion of ingredient (11), and the resultant mixture was heated to 70° C. (aqueous phase). Oily ingredients (1) through (6) were heated to melt, followed by addition of ingredient (7) thereto, and the resultant mixture was maintained at 70° C. The thus-prepared oily mixture was gradually added to the aqueous phase for preliminary emulsification, followed by treatment with a homogenizing mixer, to thereby yield emulsion particles of uniform size (emulsion part).

In the remaining portion of ingredient (11), ingredients (9), (10), and (12) through (14) were dissolved at 90° C., and subsequently, the resultant mixture was cooled to form a gel. The thus-obtained gel was thoroughly pulverized with a homogenizing mixer, to thereby yield a microgel (mean particle size: 80 μm). The microgel was added to the above-prepared emulsion part, and the resultant mixture was subjected to mixing under stirring, deaeration, filtration, and cooling, to thereby yield a massage cream (O/W).

Example 35

Hair-Setting Gel

| Ingredient | Amount (mass %) |
|---|---|
| (1) Carboxyvinyl polymer | 0.7 |
| (2) Polyvinyl pyrrolidone | 2.0 |
| (3) Glycerin | 3.0 |
| (4) Sodium hydroxide | suitable amount |
| (5) Hydrochloric acid | suitable amount |
| (6) Ethanol | 5.0 |
| (7) Curdlan | 1.0 |
| (8) Xanthan gum | 0.2 |
| (9) Polyoxyethylene octyldodecyl ether | suitable amount |
| (10) Perfume | suitable amount |
| (11) Chelating agent | suitable amount |
| (12) Purified water | balance |

<Preparation Method>

Ingredient (1) was dispersed in a mixture consisting of ingredient (3) and a portion of ingredient (12) so as to form a dispersion. Ingredient (2), a portion of ingredient (4), ingredient (6), and ingredients (9) through (11) were dissolved in the remaining portion of ingredient (12), and the resultant mixture was added to the above-prepared dispersion, yielding a mixed solution. Ingredient (7) was dissolved in the remaining portion of (4), ingredient (8) was added thereto and dissolved therein, and the mixture was neutralized with ingredient (5). The resultant neutral solution was added to the aforementioned mixed solution, and heated at 80° C. for 10 minutes. Subsequently, the formed gel was subjected to pulverizing with a homogenizer (mean particle size: 80 μm), filtration, deaeration, and cooling, to thereby yield a hair-setting gel.

Example 36

O/W Cream

| [Emulsion part E] | |
|---|---|
| Ingredient | Amount (mass %) |
| (1) Stearic acid | 8.0 |
| (2) Stearyl alcohol | 4.0 |
| (3) Butyl stearate | 6.0 |
| (4) Propylene glycol | 5.0 |
| (5) Glyceryl monostearate | 2.0 |
| (6) Potassium hydroxide | 0.4 |
| (7) Purified water | balance |

<Preparation Method>

To an aqueous phase (a mixture of ingredients (6) and (7)), the remaining ingredients were added, followed by mixing under stirring, to thereby yield emulsion part E.

The thus-prepared emulsion part E (30 mass %), caffeine (1 mass %), and viscosity control agent A prepared in Example 27 (69 mass %) were mixed, to thereby yield an O/W cream.

Example 37

O/W Cream

| [Emulsion part F] | |
|---|---|
| Ingredient | Amount (mass %) |
| (1) Solid paraffin | 5.0 |
| (2) Beeswax | 10.0 |
| (3) Vaseline | 15.0 |
| (4) Liquid paraffin | 41.0 |
| (5) 1,3-Butylene glycol | 4.0 |
| (6) Glyceryl monostearate | 2.0 |
| (7) POE(20) sorbitan monolaurate | 2.0 |
| (8) Boric acid | 0.2 |
| (9) Purified water | balance |

<Preparation Method>

To an aqueous phase (a mixture of ingredients (8) and (9)), the remaining ingredients were added, followed by mixing under stirring, to thereby yield emulsion part F.

The thus-prepared emulsion part F (70 mass %), aspartic acid (1 mass %), and viscosity control agent A prepared in Example 27 (29 mass %) were mixed, to thereby yield an O/W cream.

Example 38

Pack

[Emulsion part G]

| Ingredient | Amount (mass %) |
|---|---|
| (1) Polyvinyl acetate emulsion | 15.0 |
| (2) Polyvinyl alcohol | 10.0 |
| (3) Sorbitol | 5.0 |
| (4) Polyethylene glycol (PEG 400) | 5.0 |
| (5) Jojoba oil | 4.0 |
| (6) POE sorbitan monostearate | 1.0 |
| (7) Titanium oxide | 5.0 |
| (8) Talc | 10.0 |
| (9) Ethanol | 10.0 |
| (10) Purified water | 37.0 |

<Preparation Method>

To an aqueous phase (a mixture of ingredients (9) and (10)), the remaining ingredients were added, followed by mixing under stirring, to thereby yield emulsion part G.

The thus-obtained emulsion part G (80 mass %), dipotassium glycyrrihizinate (0.5 mass %), and viscosity control agent A prepared in Example 27 (19.5 mass %) were mixed, to thereby yield a pack.

The external compositions of the present invention prepared in Examples 33 through 38 were found to be endowed with excellent viscosity increasing property, and provided refreshing sensation during use with no sticky sensation. Moreover, the compositions were found to exhibit excellent long-term stability.

Example 39, Comparative Example 16

O/W Cream

| Ingredient | Amount (mass %) |
|---|---|
| (1) Squalane | 10.0 |
| (2) Vaseline | 5.0 |
| (3) 1,3-Butylene glycol | 4.0 |
| (4) Glyceryl monostearate | 2.0 |
| (5) POE(20) sorbitan monolaurate | 2.0 |
| (6) Agar | 1.5 |
| (7) Keltrol | 0.2 |
| (8) Purified water | balance |

<Preparation Method 1>

Ingredients (3) through (7) were added to ingredient (8), and the resultant mixture was heated to 90° C. to dissolve. The solution was continuously stirred, and ingredients (1) and (2) were added thereto at 70° C. The thus-obtained mixture was cooled under stirring to room temperature, to thereby yield an O/W cream.

<Preparation Method 2>

Ingredients (3), (6), and (7) were added to ingredient (8) (50 mass %), and the mixture was heated to dissolve, then cooled for gelation. The resultant gel was pulverized, to thereby yield a paste-like aqueous gel (mean particle size: 80 μm). The thus-prepared paste-like aqueous gel was mixed thoroughly with an O/W cream; which had been prepared by addition of ingredients (4) and (5) to the remaining portion of ingredient (8) followed by further addition of ingredients (1) and (2) thereto at 70° C., to thereby yield an emulsified product (O/W cream).

The viscosity (25° C.) of each of the O/W creams prepared through preparation method 1 or 2 was measured by use of a B-type viscometer. The viscosity of the O/W cream prepared through preparation method 1 and that through preparation method 2 were found to be 140,000 mPa·s and 300,000 mPa·s, respectively. Thus, it has been confirmed that even though the composition per se is identical, a compositional system including microgel obtained through pulverization of a gel exhibits excellent viscosity increasing property as compared with a compositional system including no such microgel.

Example 40

Moisturizing Gel

| Ingredient | Amount (mass %) |
|---|---|
| (1) Purified water | balance |
| (2) Agar | 2.0 |
| (3) Dipropylene glycol | 10.0 |
| (4) Trimethylglycine | 5.0 |
| (5) Hyaluronic acid | 0.1 |
| (6) Sodium polyacrylate | 0.2 |
| (7) Polyacrylamide | 0.5 |
| (8) Silica powder | 1.0 |
| (9) EDTA | suitable amount |
| (10) Citric acid | suitable amount |
| (11) Perfume | suitable amount |
| (12) Preservative | suitable amount |

<Preparation Method>

Ingredients (2) through (7) and (9) through (12) were added to ingredient (1), and the resultant mixture was caused to dissolve at a temperature of not lower than 85° C. Subsequently, the solution was allowed to cool to a temperature equal to or below 30° C. for solidification. Ingredient (8) was added thereto, followed by pulverization with a homogenizer to thereby yield a microgel (mean particle size: 40 μm). The thus-prepared microgel was homogeneously dispersed, to thereby yield a moisturizing gel.

Example 41

Moisturizing Cream

| Ingredient | Amount (mass %) |
|---|---|
| (1) Purified water | balance |
| (2) Agar | 1.5 |
| (3) Dipropylene glycol | 10.0 |
| (4) Xylitol | 5.0 |
| (5) Hyaluronic acid | 0.1 |
| (6) Polyacrylamide | 0.5 |
| (7) Cyclic silicone | 5.0 |
| (8) Squalane | 5.0 |
| (9) Acrylic acid/ Alkyl acrylate copolymer | 0.2 |
| (10) EDTA | suitable amount |
| (11) Triethanolamine | suitable amount |
| (12) Citric acid | suitable amount |
| (13) Perfume | suitable amount |
| (14) Preservative | suitable amount |

<Preparation Method>

Ingredients (2) through (6), (10), (12), and (14) were added to a portion of ingredient (1), and the resultant mixture was caused to dissolve at a temperature of not lower than 85° C. The solution was allowed to cool to a temperature equal to or below 30° C. for solidification. The solid was thoroughly pulverized with a homogenizer, to thereby yield a microgel (mean particle size: 70 µm). To the resultant microgel, an emulsified product which had been prepared through addition of ingredient (11) to a homogeneously dispersed mixture of ingredients (7) through (9), and (13) in the remaining portion of ingredient (1) followed by a treatment with a homogenizing mixer to obtain a homogenous emulsion was added, and subsequently, the thus-obtained mixture was subjected to homogeneous dispersion, to thereby yield a moisturizing cream.

Example 42

Pack

| Ingredient | Amount (mass %) |
| --- | --- |
| (1) Purified water | balance |
| (2) Agar | 1.5 |
| (3) Glycerin | 15.0 |
| (4) Polyethylene glycol (PEG 300) | 5.0 |
| (5) Montmorillonite | 3.0 |
| (6) Spherical resin powder (Poly(alkyl acrylate)) | 3.0 |
| (7) Zinc white | 1.0 |
| (8) Glycyrrhizic acid salt | suitable amount |
| (9) Xanthan gum | 0.2 |
| (10) EDTA | suitable amount |
| (11) Lactic acid | suitable amount |
| (12) Perfume | suitable amount |
| (13) Preservative | suitable amount |

<Preparation Method>

Ingredients (2) through (4) and (8) through (13) were added to ingredient (1), and the resultant mixture was caused to dissolve at a temperature of not lower than 85° C. The solution was allowed to cool to a temperature equal to or below 30° C. for solidification. The solid was thoroughly pulverized with a homogenizer to thereby form a microgel (mean particle size: 60 µm). To the resultant microgel, ingredients (5) through (7) were added and the resultant mixture was dispersed homogeneously, to thereby yield a pack.

Example 43

Eye Gel

| Ingredient | Amount (mass %) |
| --- | --- |
| (1) Purified water | balance |
| (2) Agar | 2.0 |
| (3) Glycerin | 10.0 |
| (4) Polyvinyl alcohol | 1.0 |
| (5) Polyacrylamide | 0.2 |
| (6) Trimethylsiloxysilicate | 1.0 |
| (7) Dimethylpolysiloxane | 5.0 |
| (8) Sodium chloride | 0.5 |
| (9) Acrylic acid/ Alkyl acrylate copolymer | 0.1 |
| (10) EDTA | suitable amount |
| (11) Citric acid | suitable amount |

-continued

| Ingredient | Amount (mass %) |
| --- | --- |
| (12) Perfume | suitable amount |
| (13) Preservative | suitable amount |

<Preparation Method>

Ingredients (2) through (5), (8), (10), (11), and (13) were added to a portion of ingredient (1), and the resultant mixture was caused to dissolve at a temperature of not lower than 85° C. The solution was allowed to cool to a temperature equal to or below 30° C. for solidification. The solid was thoroughly pulverized with a homogenizer, to thereby form a microgel (mean particle size: 70 µm). To the resultant microgel, a homogeneously dispersed mixture which had been prepared through addition of ingredients (6), (7), (9), and (12) to the remaining portion of ingredient (1) followed by dispersion with a homogenizing mixer was added, and subsequently, the thus-obtained mixture was subjected to further dispersion, to thereby yield an eye gel.

Example 44

Jelly Pack

| Ingredient | Amount (mass %) |
| --- | --- |
| (1) Purified water | balance |
| (2) Agar | 1.5 |
| (3) Butylene glycol | 10.0 |
| (4) Ethanol | 12.0 |
| (5) Polyacrylamide | 0.2 |
| (6) Carboxyvinyl polymer | 0.5 |
| (7) Sodium chloride | 0.5 |
| (8) Potassium hydroxide | suitable amount |
| (9) EDTA | suitable amount |
| (10) Citric acid | suitable amount |
| (11) Perfume | suitable amount |
| (12) Preservative | suitable amount |

<Preparation Method>

Ingredients (2) through (12) were added to ingredient (1), and the resultant mixture was caused to dissolve at a temperature of not lower than 85° C. The solution was allowed to cool to a temperature equal to or below 30° C. for solidification. The solid was thoroughly pulverized with a homogenizer for formation of microgel (mean particle size: 80 µm), to thereby yield a jelly pack.

The external compositions of the present invention prepared in Examples 40 through 44 were found to be endowed with excellent viscosity increasing property, and provided refreshing sensation during use with no sticky sensation. Moreover, the compositions were found to exhibit excellent long-term stability.

Example 45

Two-Agent Type Hair Manicure (Acid Hair Dye)

| Ingredient | Amount (mass %) |
| --- | --- |
| [Agent 1] | |
| Ethanol | 16.0 |
| Purified water | to 40.0 |
| Benzyl alcohol | 8.0 |

-continued

| Ingredient | Amount (mass %) |
| --- | --- |
| Glycolic acid | 1.6 |
| Sodium lactate (50%) | 0.6 |
| Colorant | 0.06 |
| [Agent 2] | |
| Ethanol | 4.0 |
| Purified water | to 60.0 |
| Agar (Ina Agar AX100) | 2.0 |
| Methylparaben | suitable amount |

<Preparation Method>

Agent 1: Ethanol and benzyl alcohol were mixed with purified water. To the resultant mixture, glycolic acid and sodium lactate were dissolved, and the colorant was added thereto and caused to dissolve, to thereby yield an agent 1.

Agent 2: Agar was dissolved in purified water (75° C.). Methylparaben and ethanol were added to the resultant solution, and the mixture was allowed to stand for 12 hours at room temperature. The thus-solidified agar gel was pulverized with a high speed mixer (mean particle size: 70 µm), to thereby yield an agent 2 (an agar microgel).

The acid hair dye prepared from mixing the agents 1 and 2 was found to exhibit satisfactory viscosity stability and adhesion, and was also found to have excellent sensation during use.

Example 46

One-Agent Type Hair Manicure (Acid Hair Dye)

| Ingredient | Amount (mass %) |
| --- | --- |
| Purified water | to 100.0 |
| 1,3-Butylene glycol | 20.0 |
| Benzyl alcohol | 8.0 |
| Glycolic acid | 0.2 |
| Colorant | suitable amount |
| Hydroxyethylcellulose | 0.5 |
| Agar (Ina Agar AX100) | 2.0 |
| Amino-denatured silicone | 0.5 |
| Methylpolysiloxane (20cs) | 0.1 |
| Stearyl trimethyl ammonium chloride | 0.1 |

<Preparation Method>

Agar was dissolved in a portion of purified water (75° C.). The solution was allowed to cool to 60° C., followed by addition of 1,3-butylene glycol, benzyl alcohol, glycolic acid, and hydroxyethylcellulose thereto. The mixture was caused to dissolve, and subsequently the resultant solution was allowed to stand for 12 hours at room temperature. The solidified agar gel was pulverized with a high speed mixer until a microgel having a mean particle size of 50 µm was yielded. The colorant dissolved in another portion of purified water was added to the thus-obtained microgel, and finally, amino-denatured silicone, methylpolysiloxane (20 cs), and the remaining portion of purified water in which stearyl trimethyl ammonium chloride had been dissolved were added thereto, to thereby yield an acid hair dye.

The acid hair dye prepared in Example 46 was found to exhibit high viscosity stability and adhesion, and was found to be endowed with excellent sensation during use.

INDUSTRIAL APPLICABILITY

The microgel of the present invention does not exhibit even slightest spinnability, which is unique to polymer solutions conventionally used as viscosity control agents, and an external composition containing the microgel provides a very refreshing sensation during use. Although polymer solutions may in some cases be affected by a pharmaceutical ingredient or salt incorporated therein, to thereby cause a reduced viscosity and limitation in terms of pharmaceutical ingredients or salts which can be incorporated, the microgel of the present invention does not involve such problems, and a broad range of external compositions, including cosmetic compositions, can be prepared by use of the microgel.

The invention claimed is:

1. A process for producing a viscosity control agent, the process comprising the steps of:
    dissolving agar in an aqueous solvent through heating, so as to form a resultant mixture,
    causing the resultant mixture to form a gel by stopping heating of the resultant mixture after dissolving, and then allowing the resultant mixture to stand still until the temperature of the mixture becomes lower than the gelation temperature, and
    pulverizing the gel into a microgel having a mean particle size of 0.1-1,000 µm, to thereby obtain a viscosity control agent.

2. The process according to claim 1, wherein the agar and a viscosity increasing compound incapable of forming a gel are dissolved in the aqueous solvent, said viscosity increasing compound incapable of forming a gel being one or more viscosity increasing compounds selected from the group consisting of xanthan gum, succinoglycan, polyacrylic acid, polyethylene glycol, polyacrylamide, and a polyalkylacrylamide/polyacrylamide copolymer.

3. The process according to claim 1, wherein the gel is pulverized into a microgel having a mean particle size of 1 to 300 µm.

4. The process according to claim 2, wherein the gel is pulverized into a microgel having a mean particle size of 1 to 300 µm.

5. A viscosity control agent obtained by the process of claim 1.

6. The viscosity control agent according to claim 5, which has a viscosity of 2,000-1,000,000 mPa·s at 25° C.

7. A viscosity control agent obtained by the process of claim 2.

8. The viscosity control agent according to claim 7, which has a viscosity of 2,000-1,000,000 mPa·s at 25° C.

9. An external composition comprising the viscosity control agent of claim 5.

10. The external composition according to claim 9, further comprising a pharmaceutical ingredient and/or a salt.

11. The external composition according to claim 10, wherein the pharmaceutical ingredient is one or more pharmaceutical ingredients selected from the group consisting of vitamins, anti-inflammatory agents, antibacterial agents, and whitening ingredients.

12. The external composition according to claim 10, wherein the pharmaceutical ingredient and/or the salt is contained in an amount of 0.1 to 20 mass % of the total of the composition.

13. The external composition according to claim 9, which is a cosmetic composition.

14. The external composition according to claim 9, which is a hair dye.

15. An external composition comprising the viscosity control agent of claim 7.

16. The external composition according to claim 15, further comprising a pharmaceutical ingredient and/or a salt.

17. The external composition according to claim 16, wherein the pharmaceutical ingredient is one or more pharmaceutical ingredients selected from the group consisting of vitamins, anti-inflammatory agents, antibacterial agents, and whitening ingredients.

18. The external composition according to claim 16, wherein the pharmaceutical ingredient and/or the salt is contained in an amount of 0.1 to 20 mass % of the total of the composition.

19. The external composition according to claim 15, which is a cosmetic composition.

20. The external composition according to claim 15, which is a hair dye.

* * * * *